United States Patent [19]

Schmidt

[11] Patent Number: 5,100,661
[45] Date of Patent: Mar. 31, 1992

[54] METHOD FOR REGULATING CELLULAR SIGNAL TRANSDUCING SYSTEM

[75] Inventor: Geoffrey J. Schmidt, Norwell

[73] Assignee: Eye Research Institute of Retina Foundation, Boston, Mass.

[21] Appl. No.: 170,737

[22] Filed: Mar. 21, 1988

[51] Int. Cl.$^5$ ................ A61K 39/395; A61K 9/127; C12N 5/06; C12N 1/38
[52] U.S. Cl. ................ 4234/85.8; 424/450; 435/244; 435/240.2; 530/388.26
[58] Field of Search ............. 424/94.61, 95.45, 85.8, 424/94.3; 514/866, 45, 2, 21; 530/350, 849, 387; 829/435; 436/188, 200, 244, 240.2

[56] References Cited

U.S. PATENT DOCUMENTS 4,820,631  4/1989  Lacal et al. ................ 530/387
4,870,161  9/1989  Spiegel ................ 530/328

OTHER PUBLICATIONS

Hurley et al., Science, vol. 226 (1984) pp. 860–862.
Liu et al., Biol. Abstracts, vol. 75 (1982) 68848.
Berridge (1983) Scientific American, pp. 142–152.
Schmidt et al. (Mar. 1983) A.R.V.O. Abstract.
Kahn et al., (1984) The Journal of Biological Chemistry 259:6228–6234.
Kahn et al. (1984) The Journal of Biological Chemistry 259:6235–6240.
Schmidt et al., (Mar. 1984) A.R.V.O. Abstract.
Schmidt et al. (Mar. 1985) A.R.V.O. Abstract.
Berridge (1986) *Phosphoinositides and Receptor Mechanisms* copyright 1986 by Alan R. Liss, Inc., pp. 25–45.
Whitman et al., (1986) Phosphoinositides and Receptor Mechanism, copyright 1986 by Alan R. Liss, Inc., pp. 197–217.
Kahn et al. (1986) The Journal of Biological Chemistry 261:7906–7911.
Payne et al., (1986) J. Gen. Physiol. 88:127–142.
Schmidt et al., (Mar. 1986) A.R.V.O. Abstract.
Greene et al., (1987) Seminars in Medicine of the Beth Israel Hospital, Boston 316:599–606.
Cockcroft (1987) Trends in Biochemical Sciences 12:75–78.

*Primary Examiner*—Jacqueline Stone
*Attorney, Agent, or Firm*—Lahive & Cockfield

[57] ABSTRACT

Disclosed is a method of inhibiting inositol metabolism in a cell. This method includes introducing into a cell a binding molecule which reduces inositol metabolism by reacting with A-protein or an A-protein containing complex. The binding molecule is an antibody which may be introduced into the cell via a liposome.

2 Claims, 5 Drawing Sheets

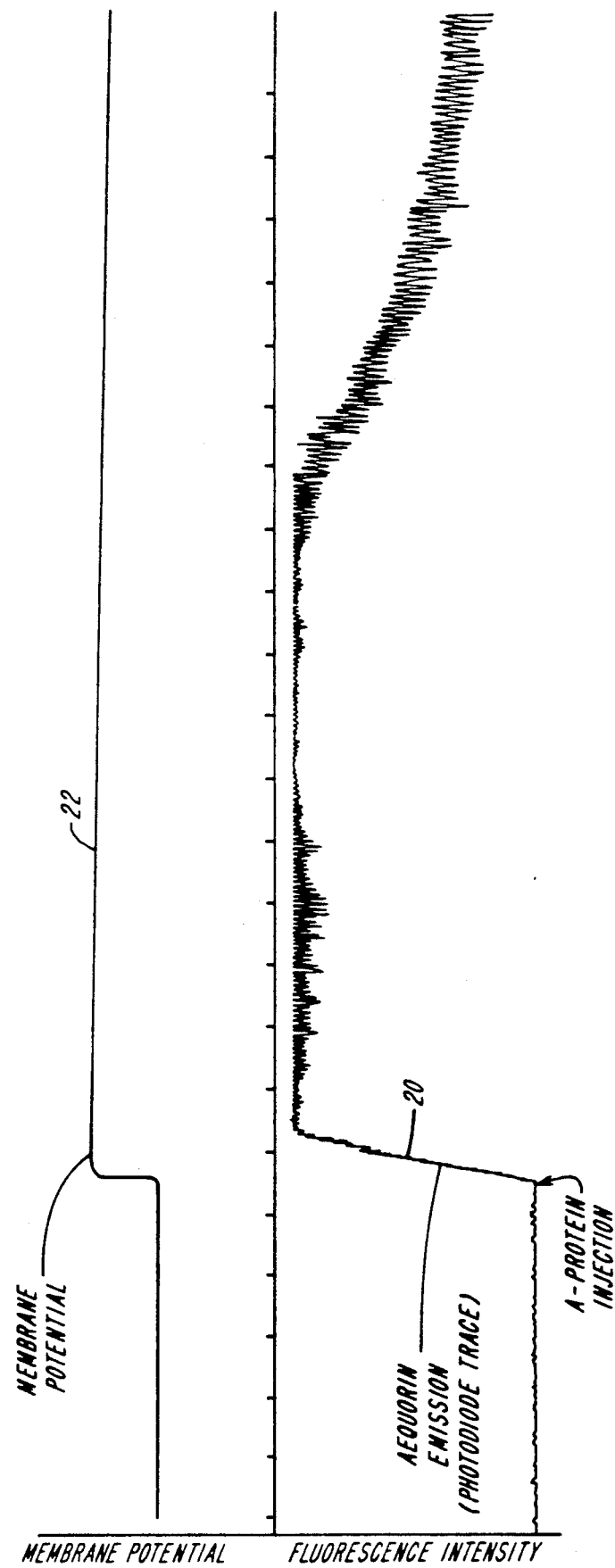

METHOD FOR REGULATING CELLULAR SIGNAL TRANSDUCING SYSTEM

BACKGROUND OF THE INVENTION

Fundamental to the response of cells to external stimuli is the stimulation of cell surface receptors by external signals. While there are a number of different receptors embedded within the plasma membrane, and a variety of such external signals, e.g., hormones, blood and growth factors, neurotransmitters, and radiation of a specific wavelength, there is a limited number of internal signals or second messengers employed within the cell. A second messenger is one that activates an appropriate cellular response to a specific external signal. It becomes activated when the receptor stimulated by an external signal excites an internal enzyme, which in turn stimulates the production of a second messenger substance.

An early signal transduction system identified in the art was the beta adrenergic receptor-adenylate cyclase pathway. This system employs the second messenger cyclic adenosine monophosphate (cAMP), a derivative of adenosine triphosphate (ATP). Its mechanism of action is now understood to proceed as follows: the external signal-receptor complex interacts with a guanosine nucleotide binding protein called a G-protein. G-protein activates adenylate cyclase, which in its activated form can catalyze the production of the second messenger, cAMP, from ATP. cAMP, in turn, causes cellular activity, e.g., protein synthesis, secretion, cytoskeletal movement, constituting a cellular response.

G-proteins are a class of regulatory proteins which bind guanosine di- and triphosphate nucleotides, i.e., GDP and GTP, respectively. The family of G-proteins serves as peripherally membrane-bound signal transducing polypeptides (STPs), coupling activation of cell surface receptors to the regulation of intracellular effectors. These proteins can activate the enzymatic abilities of adenylate cyclase or a phosphodiesterase while binding GTP. Examples of known and probable G-proteins include $G_s$ and $G_i$, which are responsible for the regulation of adenylate cyclase; transducin, which activates a cGMP-specific phosphodiesterase in the retina; ADP-ribosylation factor (ARF) in the liver (Kahn et al. J. Biol. Chem. 259:6228-6234, 1984); and P21, the product of the ras protooncogene. (For a review, see Whitman et al., *Phosphoinositides and Receptor Mechanisms*, copyright 1986 by Alan R. Liss, Inc. pp. 197-217).

A second signal transduction system serves as a basis for cellular signalling by mitogenic growth factors such as growth hormone (GH), platelet-derived growth factor (PDGF), epidermal growth factor (EGF), and radiation of specific wavelengths. This system involves various intermediates in the inositol metabolic pathway. It employs calcium ions and a combination of second messengers ultimately derived from phosphatidylinositol (PI), which is a minor plasma membrane constituent. In this system an external signal, such as light in the photoreceptor cell, activates a receptor, e.g., rhodopsin, which then, by means heretofore unknown, stimulates the catalytic activity of phospholipase-C. A key event with regard to the second messenger function is the hydrolysis of an inositol derivative, phosphatidylinositol 4,5-biphosphate (PIP$_2$), a minor membrane constituent, by phospholipase-C (PL-C) to yield inositol-1,4,5-trisphosphate (IP$_3$) and diacylglycerol (DG). Both of these reaction products act as second messengers in at least two different systems: DG controls ion currents through the membrane by regulating membrane permeability to various ions and the activity of protein kinase C; while IP$_3$ regulates the concentration of intracellular $Ca^{+2}$ which in turn affects many cellular processes, e.g., cell division and proliferation Because of the intimate involvement of the inositol metabolic pathway in this second messenger system, it is understood that failure in the pathway mediate the development of a number of disease states. For example, there is now a large body of evidence supporting the concept that the secondary effects of diabetes, i.e., vascular degeneration and slowed nerve conduction, are the result of stepped-up sorbitol production that results from a failure of the inositol metabolic pathway. The effect of chronically high blood sugar levels on the inositol pathway is to retard inositol metabolism. This may be the result of the inactivity of a regulatory G-type protein due to the glycosylation of nuclear elements, e.g., genes or regulatory proteins, or be the result of the direct glycosylation of the G-type regulatory protein.

Retinitis pigmentosa, a disease of the eye characterized by toxic levels of unmetabolized GTP in photoreceptors, may result from a failure of GTP hydrolysis, due to absent or reduced levels of GTPase activity of a G-protein, or by the inability of a mutated G-protein to bind or mediate hydrolysis of GTP.

Current evidence suggests that at least some types of human cancer, or uncontrolled cell proliferation, are the result of a mutation in a regulatory enzyme of the inositol system. The suspected mutation is understood to prevent the hydrolysis of GTP, the inactivating step for the entire inositol metabolic pathway, including systems initiated by growth hormone (GH). If the inositol system is unable to shut off, the result is uncontrolled cell division, or malignancy. Alternatively, the malignant state could result from the hyperproduction of IP-3 caused by the overproduction, or faulty production, of an enzyme controlling the inositol pathway.

Disease states characterized by the lack of cell division, i.e. lack of proliferation, can also be the result of a failure in the inositol-related signal transduction system to increase intracellular $Ca^{+2}$ levels, or to respond to GH or other growth factors.

Accordingly, the elucidation of the regulatory mechanism involved in the inositol-related signal transduction system will provide a better understanding of the disease states which result from its dysfunction, and can lead to the development of Preventative and/or compensatory measures. More specifically, there exists a need for methods of treating disease states resulting from the dysfunction of this system, and for methods of regulating inositol metabolism in cultured cells and cells of higher organisms.

Therefore, it is an object of this invention to provide proteins linking functionally cell membrane receptors and the inositol-related signal transducing system. It is also an object to provide a method of regulating the inositol metabolic pathway to compensate for disease states resulting from its dysfunction. Another object is to provide a method of stimulating and of depressing the inositol metabolic pathway in cell cultures and multicellular organisms.

These and other objects of the invention will be apparent from the description, drawing, and claims which follow.

SUMMARY OF THE INVENTION

It has now been discovered that an intracellular enzyme, called A-protein, is responsible for the regulation of the inositol-related signal transducing system. In this system, A-protein functions by activating PL-C to generate the second messengers $IP_3$ and DG. Upon stimulation of a membrane bound receptor, A-protein binds with GTP to form an intermediate which functions to activate PL-C. When the GTP of the intermediate is hydrolyzed to GDP, PL-C activation terminates. A-protein is accordingly an important G-type signal transducing polypeptide (STP) critical to proper functioning of the cellular inositol metabolic pathway.

This knowledge has been exploited to develop methods for regulating metabolic pathways that include the involvement of PL-C and/or $IP_3$ and DG messengers, or more directly, of A-protein, itself and to provide novel bioactive compositions which stimulate, inhibit, or normalize inositol metabolism in cells.

For example, the inositol metabolic pathway in a cell can be sensitized by introducing an STP into that cell, e.g., by means of a liposome. The inositol pathway may be stimulated by the introduction of preactivated A-protein, e.g., an A-protein-GTP conjugate, preferably comprising a non hydrolyzable GTP analog, e.g., a commercially available material such as GTP gamma S or GMPPNP. The STP useful in these methods of the invention has the ability to functionally couple an activated membrane-bound receptor to a phosphodiesterase, which then becomes enzymatically active. The phosphodiesterase is the enzyme responsible for generating a second messenger that causes a cellular response.

The STP useful in the foregoing methods of the present invention are A-protein, an active fragment of A-protein, an A-protein analog, or a fusion protein or derivative of A-protein. Incubation of these materials with non-hydrolyzable GTP analogs, or other complexes of the two, provide inositol metabolism stimulants.

A-protein itself has a molecular weight of about 20–21 kD and has a significantly hydrophobic region. It also has the ability to bind and hydrolize guanosine nucleotides. Further characterizations of the STP, for the practice of the invention, are that it comprise a single polypeptide chain, has the ability to bind and hydrolyze adenosine and guanosine triphosphate, and has the ability to activate phospholipase C and other phospholipases in the presence of GTP. Native A-protein may be recovered from known and available cells, e.g., photoreceptor cells of the eye, and many other cell types. Native A-protein can be obtained in purities greater than 80% from vertebrate photoreceptors and other types of cells using the methods disclosed below. The stability of A-protein in aqueous suspension is enhanced by the addition of nonionic detergents.

The membrane-bound receptor which activates the STP may be one which is responsive to mitogenic signals such as hormones, growth factors, radiation of a particular wavelength, or neurotransmitters.

Additionally, the metabolic pathway of inositol in a cell, in further accord with the invention, can be inactivated or inhibited by the introduction to that cell of an antibody which binds an STP such as A-protein, an active fragment, analog, or fusion product thereof. The antibody may be a monoclonal antibody, and may be administered via a liposome. A similar effect can be achieved using an enzymatically non-functional A-protein analog which competes with native A-protein with the effect of reducing the level of inositol metabolism. Such a construct retains the ability of A-protein to interact with a membrane-bound receptor or with GTP, but has lost the ability to activate PL-C.

The present invention provides a method of stimulating the proliferative abilities of a cell. This method comprises the step of introducing into the cell an STP as characterized above conjugated with a non-hydrolyzable analog of GTP. Conversely, cell proliferation can be inhibited by introducing an antibody which recognizes, binds, and inactivates the STP, as characterized above, or by introducing a non-functional A-protein analog.

Further, the present invention provides a method for controlling secondary effects of diabetes, including vascular degeneration and slowed nerve conduction and a method of reducing the intracellular concentration of GTP. These methods comprise introducing into the cells of a subject an STP as characterized above.

Lastly, the invention provides novel compositions of matter, useful for stimulating the inositol metabolic pathway in a cell, and for promoting cell proliferation, consisting of A-protein, an active fragment, analog, or fusion product thereof, coupled to a non-hydrolyzable GTP analog, e.g., guanosine-5'-O-[3 thiotriphosphate] or B-γ-imidoguanosine 5' triphosphate.

BRIEF DESCRIPTION OF THE DRAWINGS

The foregoing and other objects of this invention, the various features thereof, as well as the invention itself, may be more fully understood from the following description, when read together with the accompanying drawings, in which:

FIGS. 3A and 3B are graphs of the electrical response and light emission of an aequorin-laden Limulus photoreceptor cell to light stimuli without treatment with A-protein (4A) and to a Limulus photoreceptor cell injected with a preactivated A-protein (4B)

DESCRIPTION OF THE INVENTION

The protein responsible for the regulation of the inositol-related signal transducing system has now been discovered. This new STP, named A-protein, has the ability to hydrolyze ATP and GTP, and therefore constitutes an ATPase and GTPase. It also has the ability to activate phospholipases including phospholipase C, phospholipase D, and possibly also phospholipase $A_2$.

Figure 1:
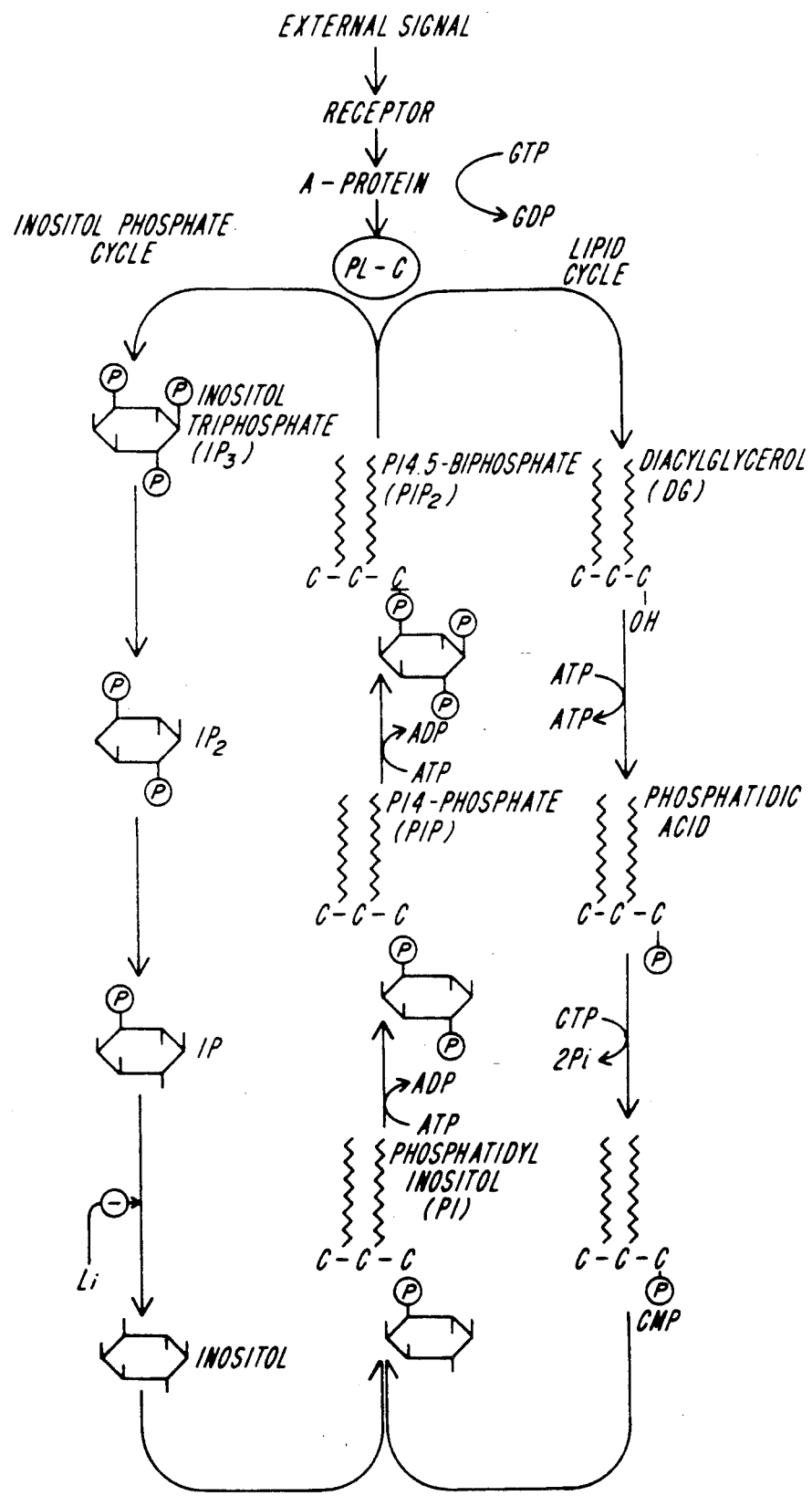
FIG. 1 is a schematic representation of the known inositol lipid metabolic pathway that yields second messengers $IP_3$ and DG, supplemented to show the function of A-protein.

FIG. 1 shows the inositol-lipid metabolic pathways which provide these second messengers. As illustrated, A-Protein is directly responsible for the activation of PL-C which catalyzes the production of second messengers $IP_3$ and DG from $PIP_2$, which is an inositol and lipid derivative. Upon activation of a receptor, A-protein present on or about the interior of the cell membrane binds with GTP. This complex activates PL-C, which in turn acts on $PIP_2$ to yield second messengers $IP_3$ and DG. The stimulating activity of the A-protein-GTP complex ceases upon hydrolysis of GTP which is then released as GDP.

A-protein present within an animal cell is inactive in the absence of receptor stimulation, but addition increases sensitivity to receptor stimulation. Accordingly, a cell which expresses a mutant form of A-protein with reduced activity may have its metabolism corrected by the introduction of A-protein or an expressable gene that encodes it. Persistant activation of the inositol pathway can be provided by introducing into a cell a conjugate of A-protein and a non hydrolyzable analog of GTP. This bypasses the necessity of receptor activation and results in persistant stimulation. Introduction of an A-protein-non hydrolyzable GTP analog conjugate can temporarily "transform" a cell, inducing cell proliferation for a limited time.

A cell's inositol metabolism may be inhibited by the introduction of a non functional A-protein analog which competes with the native form upon stimulation of a receptor. Thus, a truncated form or analog of A-protein which retains the ability to bind GTP and/or to couple with a receptor, but lacks the ability to activate PL-C inhibits inositol metabolism when introduced into a cell. Antibodies against A-protein bind and inactivate it, thus also inhibiting inositol metabolism and reducing or terminating the effect of receptor stimulation. Intracellular administration of such a non-functional analog or antibody can inhibit cell mitosis.

A-protein has been isolated from mammalian (bovine) and amphibian (frog) rod outer segments (ROS) by extraction, centrifugation, chromatography and other protein purification techniques known to those skilled in the art. Other proteins with similar or identical physical and functional characteristics as A-protein have been isolated from various other tissues from vertebrates and invertebrates. These findings indicate that the structure of A-protein has been conserved through evolution, and is now understood to indicate that A-protein has a universal regulatory role in cells which employ inositol-type metabolism. A-protein is quite labile in aqueous solution, but can be significantly stabilized if disposed in aqueous solutions containing a nonionic surfactant. It has a molecular weight in the range of 20 to 21 kD, as inferred by comparison to molecular weight standards during electrophoretic separations. Preferred methods of isolating the native protein are disclosed in detail below. Good purification results have been achieved using filters with molecular weight cutoffs in the range of 10 kD and 30 kD.

A-protein, various truncated or mutein analogs thereof, and fused proteins comprising A-protein and other protein domains can be produced by various synthetic and biosynthetic means. For example, an appropriate host cell such as a microorganism, yeast, or eucaryotic cell culture can be genetically engineered to express A-protein, or a portion or analog thereof. This may be accomplished by now well established recombinant DNA technologies known to those skilled in the art. The recombinant procedure may include the isolation or synthesis of a gene encoding an A-protein, a portion, or analog thereof, and the integration of that gene into a plasmid. The amino acid sequence of A-protein may be established readily given this disclosure. Gene synthesis from synthetic oligonucleotides and known mutagenesis techniques provide the technologies to prepare an array of analogs, truncated A-protein forms, and fused proteins comprising A-protein or a domain thereof. Production of such materials further may include the transformation of an appropriate host cell with a vector harboring the recombinant DNA, culturing that transformed host cell, and isolation of the expressed protein. Given the availability of A-protein rich samples producible as disclosed herein, the recombinant production of the native form and various analogs thereof is well within the current skill in the art.

A-protein is also useful as an antigen to produce antibody, which can be used to depress a cellular mechanism which relies on the enzymatic action of A-protein. The antibody may be a polyclonal antisera or an active portion thereof raised against A-protein, and shown to react with A-protein or to its analogs and fragments. However, the antibody is preferably a monoclonal antibody produced by methods known per se. The antibody preferably is selected not to cross-react with the cellular components. This antibody can be of any class and subclass. The anti-A-protein monoclonal immunoglobulin produced by the hybridoma preferably is of the IgG class as determined by the Ouchterlony double diffusion test.

Alternatively, the antibody which recognizes A-protein can be synthesized by biosynthetic or recombinant means, either in whole or in part, and can be linked to other functional molecules such as toxins, dyes, enzymes, or radioactive markers.

The anti-A-protein monoclonal antibody can be obtained from a hybridoma cell line formed upon the fusion of a mouse myeloma cell with a spleen cell of a mouse previously immunized with A-protein purified, for example, from bovine ROS. The immunogen alternatively can be a derivative of A-protein, or an analog or portion thereof, produced in vitro according to known mechanical or manual procedures of peptide synthesis. Alternatively, the immunogen can be synthesized by biosynthetic means using recombinant DNA technologies known to those skilled in the art. The mice whose spleen cells are chosen for fusion are preferably from a genetically defined lineage such as Balb/c. The myeloma cells used in the fusion are from a mammalian, antibody-producing cell line, but most preferably are from a mouse cell line such as, e.g., NS-1. The monoclonal antibody can be obtained from ascites fluid of mice injected with the fusion product.

The antibody so produced is specific for A-protein, and therefore is particularly useful in regulating mechanisms which involve A-protein. For example, the antibody will be useful in inhibiting the metabolism, shown in FIG. 1, of $PIP_2$ to second messengers DG and $IP_3$.

A-protein or an antibody thereto, conjugate, or analog thereof may be administered, via the use of a protective and directive vehicle such as liposomes, to a subject afflicted, for example with cancer, diabetes, retinitis pigmentosa, etc., or to a cell culture to stimulate or depress inositol metabolism. Liposomes contacting a cell membrane deposit their contents into the cell via endocytosis. Liposomes useful for this purpose can be prepared by any number of methods (e.g., Bangham et al. (1965) J. Mol. Biol. 13:238-252; Deamer and Bangham (1976) Biochem. Biophys. Acta, 443:629-634). The method of Ghalayini and Anderson (Biochem. Biophys. Res. Comm. (1984) 424:503-506) is preferred. Briefly, these methods include mixing the material to be entrapped or incorporated, e.g., A-protein, an A-protein non hydrolyzable GTP analog conjugate, or anti-A-protein antibodies, with the appropriate lipids, e.g., ROS membrane-extracted, in a buffer, and sonicating the mixture.

From the foregoing it will be apparent that compositions of the types described above have several utilities, both in vitro and in vivo. The introduction of the native or of active analog forms of A-protein into cells having an overabundance of GTP, or expressing a defective form of native A-protein, can reduce intracellular GTP concentration and restore or improve inositol metabolism. Activated A-protein conjugates can stimulate inositol metabolism, leading to cell replication. Thus, introduction of such conjugates into the cells of a transformed or non-immortal cell culture can produce a pulse of replication. Non-functional A-protein conjugates and antibodies to A-protein can depress inositol metabolism, and thus mitosis, in, for example, malignant cells.

The following examples further disclose the nature of the invention, without limiting the scope thereof.

EXAMPLES

1. Purification of A-Protein

A-protein can be isolated from the retinas of cow eyes essentially as described by Schmidt et al. (J. Biol. Chem. (1987) 262:14333-14336). Cow eyes obtained from a local abattoir within an hour of killing and enucleation are kept on ice in the dark for 1 to 1½ hours. Retinas are easily dissected away from the pigment epithelium of dark-adapted eyes, removed, and placed in Buffer A (100 mM NaCl, 20 mM Tris, 2 mM $MgCl_2$, pH 7.2) at 0.5 ml/retina on ice. Gentle shaking of the vessel results in the liberation of large numbers of ROS, broken off at the ciliary constriction, into the buffer. The mixture is poured through a ceramic Buchler funnel to remove the retinas. The resulting ROS suspension is sedimented on ice for 5 min. to allow any gross particulate matter to settle. The suspension contains >95% ROS.

To remove any remaining non-ROS contamination, the ROS suspension is spun down at 5,000 rpm in a refrigerated centrifuge for 10 minutes and the supernatant poured off. The ROS pellet is resuspended in an equal volume of Buffer A by drawing the buffer and ROS repeatedly through a 21-guage hypodermic needle. This procedure mechanically disrupts the outer segments, and allows soluble ROS constituents to be solubilized in the suspension buffer. Membranes are again spun down in a refrigerated centrifuge at 13,000 rpm for 10 minutes and the supernatant, containing soluble ROS proteins, is removed. The protein solution is placed in Centricon 30 (Amicon Corp.) ultrafiltration device which retain proteins of molecular weight over approximately 30 kD. It is then centrifuged at 6,500 rpm (5,000 X g) in a fixed-angle rotor (SS-34, Sorvall) at 0° C. Because A-protein passes through the filter upon centrifugation, it is rapidly separated from most (>85%) of the other extracted soluble proteins. The ultrafiltrate containing the enriched A-protein fraction is collected upon completion of the run (about 1 hour). It is then placed in a Centricon 10 ultrafiltration device where the retained proteins (<10 kilodaltons) are concentrated and dialyzed into Buffer B (20 mM Tris, pH 7.2, 0.1% (w/v) polyoxyethylene 23—lauryl ether (Brij 35 - a nonionic surfactant) by centrifugation (6,500 rpm at 0° C). Brij 35 is added to the dialysis buffer to decrease aggregation of A-protein.

The concentrated protein sample is applied to a Sephadex G-50 gel filtration column (2×40 cm) equilibrated with Buffer B. Use of the Centricon 30 to remove most of the >30 kD proteins greatly enhances resolution and recovery of the 20 kD A-protein peak. Running time for this column at 0°-4° C. is approximately 40 minutes (flow rate, 2 ml/min; 2 ml fractions collected). The A-protein peak is pooled and concentrated by centrifugation. Use of the centrifuge device sold under the name Centricon appears to result in better yields of recovered protein due to the limited surface area of the filter when compared with other ultrafiltration and concentration devices.

2. Limulus Photoreceptor Response Tests

*Limulus polyphemus* is one highly suitable system in which to examine the function of A-protein in a signal transducing system, because the response of its ventral photoreceptor can easily be recorded, and because its system of cellular communication is well defined and understood. The following experiments demonstrate that purified, activated A-protein is capable of activating PL-C in the Limulus photoreceptor such that second messengers are produced, and cause electrical signals to be generated in the cell in response to an external light signal. The response is characteristic of inositol metabolism stimulation in this type of cell. This interpretation is the only presently known mechanism of calcium release in Limulus ventral photoreceptors.

A. Activation of A-Protein (Preparation of A-Protein-Non Hydrolyzable GTP Conjugate)

A-protein is incubated with 1 mM of the non-hydrolyzable GTP analog guanosine -5'-0-[3-thiotriphosphate] (GTPγS)(Boehringer Mannheim) for 1 hour at 0° C. in order to activate the protein. The A-protein solution is then dialyzed on a Centricon 10 to remove free GTPγS.

B. Preparation of Limulus Photoreceptor

The ventral nerve photoreceptor cells from *Limulus polyphemus* are stripped of glial cells and placed in a dish containing gelled agarose. The nerve is held in place with dissecting pins and perfused with seawater. The viability of the preparation is established by impaling one of the photoreceptors with a glass microelectrode (filled with 100 mM K+ aspartate, 10 mM HEPES (Sigma Chemical Co., pH 7.0) and recording the response of the cell to a 10 μm spot of white light (45 W tungsten-halogen lamp (Sylvania Lighting, Danvers, Mass.) delivering 40 mWcm²).

C. A-Protein Administration

Activated A-protein is pressure-injected into ventral photoreceptors by a double-barreled glass microelectrode which impaled the A lobe of the photoreceptor. One side of the electrode is connected to an amplifier (WPI) and a chart recorder (Gould) and the other side is filled with the same solution (100 mM K$^+$ aspartate, 10 mM HEPES, pH 7.0) which contained activated A-protein ($=10$–$20$ $\mu$/ml). The barrel of the electrode containing A-protein is connected to a nanoliter pump (ECM 1400, W-P Instruments).

Injections of activated A-protein caused a rapid depolarization of the photoreceptor membrane potential. The depolarizations were from 5–25 mV (time to peak 2–10 seconds, lasting several minutes) with a smooth rising phase. The injection produced a profound and prolonged desensitization of the photoreceptor to test flashes of light lasting for 0–15 minutes after which the cells recovered to near baseline sensitivity.

Figure 2:
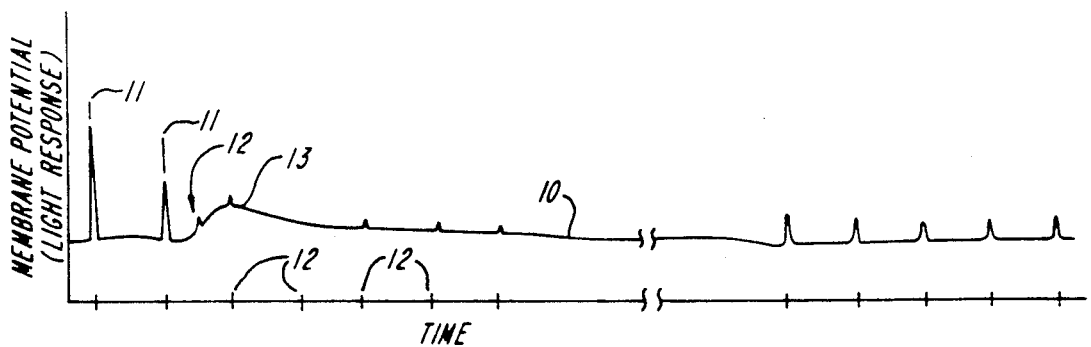
FIG. 2 is a graph of the electrical response (as indicated by membrane potential) of a Limulus photoreceptor cell to light after treatment with a preactivated A-protein, both immediately before, about a minute after, and 15 minutes after preactivated A-protein injection.

The test results of FIG. 2 indicate the light flashes with trace 10, the injection of activated A-protein at 12, and the cellular response to the light flashes, both before and after the injection. This recording shows that the injection of the A-protein caused a depolarization of the photoreceptor sufficient to essentially abolish responses to subsequent test flashes of light. The right end of the response trace 10 shows some recovery of cellular sensitivity approximately fifteen minutes after the injection. A total of seven separate cells were injected and the results were uniform, and consistent with calcium release.

Thus, upon administration of the A-protein-GTP analog conjugate, the response of the cell is altered dramatically from the normal response of a spike of depolarization (indicated at 11) to a sustained depolarization maximum 13 which decays over time. During this time, repeated light flashes activate the receptor, but the cellular response is altered significantly by the presence of the activated A-protein.

D. Aequorin Administration

To confirm that A-protein injection causes a rise in intracellular calcium, photoreceptor cells were injected with the calcium-sensitive dye aequorin (7 mg/ml). Injections of aequorin were typically 10–100 pl, injected by a series of pressure pulses. In the presence of calcium, aequorin luminesces. This luminescence was detected by a photodiode (model IIIA, United Detector Technology, Santa Monica, Calif.). Emissions from aequorin were integrated and amplified by a signal averager and recorded on one channel of a chart recorder.

Figure 3A:
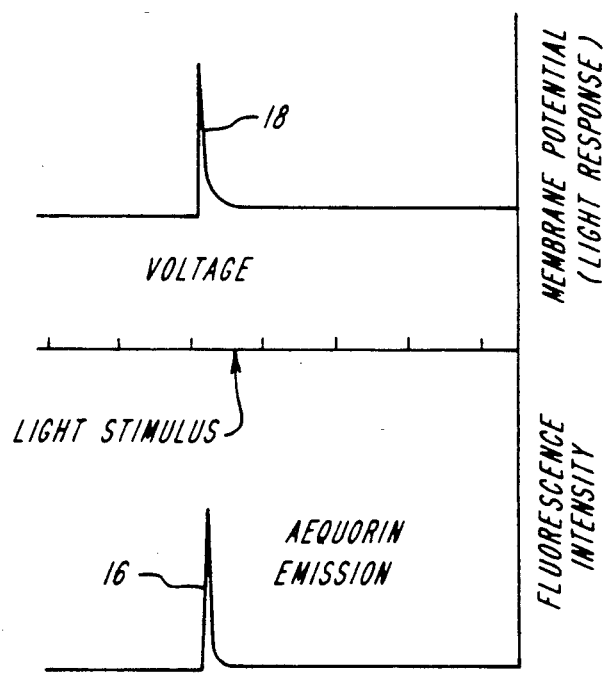

FIG. 3A shows with trace 16 the response of a photodiode monitoring the aequorin emission, under stimulation by a flash of test light. Trace 18 records the membrane potential of the cells. Both traces were made prior to injection of activated A-protein. As FIG. 3B shows, injection of activated A-protein causes the aequorin emission, trace 20, to go off-scale for a significant duration, and causes the membrane potential, trace 22, to exhibit prolonged depolarization.

In four cells, each loaded with 10 mg/ml of aequorin, injection of activated A-protein caused a slow rise in aequorin luminescence indicating a commensurate rise in internal calcium in the photoreceptor (FIG. 3B). The rise in calcium can account for the observed desensitization of the photoreceptor. Release of calcium within the Limulus ventral photoreceptor has been shown to be the result of the activation of PL-C. In addition, IP$_3$ has been shown to release calcium from internal stores in Limulus photoreceptors (Payne et al, J. Gen. Physiol., 1986 Jul; 88(1):127–42).

E. Administration of Heat-Inactivated A-Protein

Control experiments employed the activated A-protein solution used above. The solution was boiled for 10 minutes to heat-inactivate the protein before being injected into the ventral photoreceptor as above. This was used to determine that the protein, which is denatured by heat, was the cause of the observed effect, as opposed to some other soluble component of the buffer solution used as carrier for the protein.

Injections of the heat-inactivated A-protein solution into four healthy, responsive cells produced no depolarization or significant desensitization of the photoreceptor, even when 20–80 times the amount of A-protein used to elicit desensitization was injected.

Figure 3C:
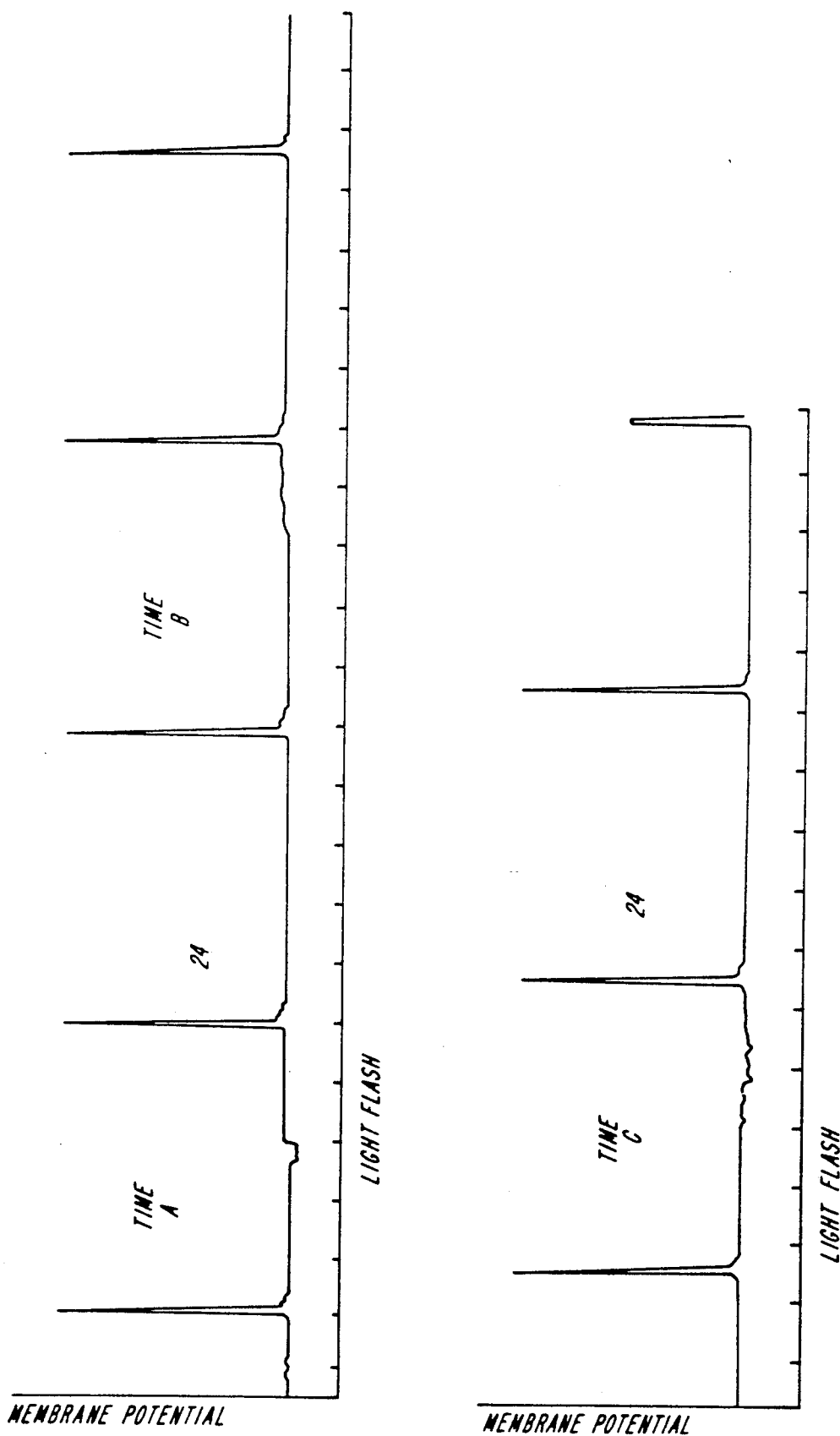
FIG. 3C is a recording of the electrical response of an aequorin-laden Limulus photoreceptor cell to treatment with multiple injections of heat-inactivated A-protein.

In particular, FIG. 3C shows with trace 24 that the membrane potential of the cells responds to flashes of light, as used in the tests of FIGS. 2 and 3A and B, without exhibiting significant depolarization or desensitization of photoreceptor cells, when the boiled A-protein is injected. This A-protein solution was injected into the cells progressively in increasing amounts, namely, two injections at Time A, three injections at Time B, and five injections at Time C.

3. Reconstitution Experiments

A. Preparation of Components

A-protein was purified as described above. A cytosolic fraction containing PL-C activity was prepared by extracting soluble proteins from ruptured ROS in buffer A (100 mM NaCl, 20 mM Tris, pH 7.0, 1 mM MgCl$_2$). This solution was washed 3 times to remove all of the A-protein with buffer B (10 mM Tris, PH 7.0, 0.1 mM EGTA) and concentrated on Centricon 30 ultrafiltration instruments. Stripped ROS membranes (containing rhodopsin as the receptor) were prepared by washing the membranes 3 times in buffer A and 3 times in water, 0.01% polyoxyethylene 23 lauryl ether (Brij 35 nonionic detergent, Sigma Chemical Co.). The stripped membranes were resuspended in buffer B (rhodopsin concentration$=100$ $\mu$M) prior to use.

B. ROS Membrane Labelling

Prior to stripping, ROS membranes were ruptured in buffer A (1 ml/retina) containing 1 mM ATP and 200 $\mu$l (50$\mu$Ci) of myo-[2-$^3$H(N)]inositol (250 $\mu$Ci/ml) (New England Nuclear, Boston, Mass.) was added. This mixture was allowed to incubate at room temperature for 3–5 hours. This resulted in significant uptake of radiolabel by the membranes as PI, phosphatidylinositol 4-phosphate (PIP), and (PIP$_2$).

C. Experimental Procedure

The stripped, radiolabelled ROS membranes (50 $\mu$l) were recombined with 30 $\mu$l of A-protein (5–8 $\mu$g) solution and the cytosolic PL-C-containing fraction in buffer B which contained 1 mM GTP, 1 mM ATP, and 0.01% nonionic surfactant. The final volume of each sample was 200 $\mu$l. In addition to these samples, control samples containing either no A-protein, no PL-C, or none of either were prepared to check the PL-C solution and ROS membranes for background activity.

Figure 4:
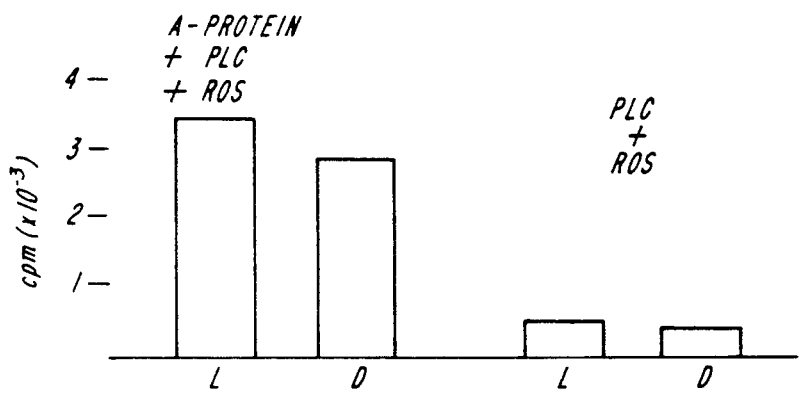
FIG. 4 is a bar graph depicting the results of reconstitution experiments in which rod outer segment (ROS) membranes, prelabelled with $^3$H-myoinositol, were reconstituted with A-protein and PL-C, and exposed to light (L) or dark (D). The release of radioactivity due to the degradation of $PIP_2$ is measured in the presence and in the absence of A-protein.

Samples were either exposed to a bright 10 μsec xenon flash (Nikon) (delivering $1.8 \times 10^3$ μWcm$^{-2}$sec$^{-1}$) sufficient to bleach >70% of the rhodopsin present in each sample or kept in the dark as control. Both dark and light samples were simultaneously quenched with 200 μl of ice cold 15% trichloroacetic acid immediately following the light flash (within 10 seconds). Following quench, the samples were kept on ice for 30 minutes. Samples were spun down in a microcentrifuge for 5 minutes and 100 μl of supernatant was aliquoted for liquid scintillation counting. The results are shown in FIG. 4. The release of radioactivity from the lipid phase of the incubation (membranes) to the aqueous phase (supernatant following spin), as the data for FIG. 4 shows, indicates activation of PL-C by A-protein and subsequent hydrolysis of $PIP_2$ to form the soluble product $IP_3$.

FIG. 4 shows the radioactivity, represented as counts per minute (cpm), recovered in the aqueous phase of ROS membrane, prelabelled with tritiated myoinositol, and reconstituted with purified A-protein and the phospholipase C ROS fraction. Bars in FIG. 4 marked "L" represent samples exposed to a xenon flash; samples represented by "D" were kept dark. The bars on the right in the drawing are for identical samples without the A-protein and hence depict background.

In this experiment, as demonstrated by FIG. 4, only the samples containing A-protein showed a specific release of radioactivity sufficient to indicate that A-protein is capable of activating PL-C in the presence of bleached rhodopsin. The high levels of activation seen in the "dark" A-protein samples may be due to stray light activation of "dark" rhodopsin combined with an excess of A-protein. Comparison of light and dark samples reveals the light-dependent component of the reaction.

3. Substrate Specificity Tests

A. Extraction of ROS Lipids

Two mls of ROS suspension were prepared from 10 bovine retinas, as previously described. The suspension was mixed with a five-fold excess of chloroform-methanol (2:1) and allowed to stand on ice for 1 hour. The mixture was spun briefly and the lower phase was removed with a pipette. This lower phase ($\approx 2$ ml) was removed and washed once with 3 mls of chloroform-methanol-0.2N HCl (3:47:48). The lower phase was removed and used as described. This solution contained=1 μM lipid/ml.

B. Preparation of Liposomes

Liposomes were prepared according to the method of Ghalayini and Anderson (supra). Purified A-protein and A-protein-free PL-C fractions were prepared as described previously. $^3$H-PIP (L-alpha-[myo-inositol-2-$^3$H(N)]) phosphatidylinositol-4,5-biphosphate; New England Nuclear, Boston, MA) was incorporate into stripped ROS membranes, prepared as described above, by means of liposomes. $^3$H-PIP$_2$ (0.5μCi) was dried under N$_2$ after being mixed with lipids extracted from ROS. Buffer B was added to the test tube containing the dried $^3$H-PIP /lipid residue and the contents of the tube were sonicated for 10 minutes in a sonicating waterbath (Branson Ultrasonic Cleaner, Shelton, Conn.). This resulted in a fine suspension (clear) of liposomes containing $^3$H-PIP$_2$. This suspension was combined with an equal volume of stripped ROS membranes suspended in buffer B (rhodopsin conc.=500 μM) and allowed to stand for 10-24 hours at 0° C.

C. Experimental Procedure $^3$H-PIP -labeled ROS membranes (100 μl) were combined with purified A-protein (5-10 μg), and A-protein-free PL-C fraction in a buffer. The buffer contained 20 mM tris, pH 7.0, 1 mM ATP, 0.25 mM GTP and 0.05 mM GMPPNP (β-γ-imidoguanosine 5'-triphosphate) (Sigma Chemical Co., St. Louis, Missouri), a non-hydrolyzable GTP analog. Each sample had a final volume of 300 μl.

Control samples were made up as above except that either A-protein or PL-C or both were deleted. Identical samples, including control samples, were either kept dark or exposed to room light for 30 minutes. Aliquots of each sample (100 μl) were removed at 1, 10, and 30 minutes of the incubation and quenched with an equal volume of ice-cold 15% trichloroacetic acid. Quenched samples were kept on ice for 30 minutes and then spun for 5 minutes in a microcentrifuge. 100 μl of the supernatant of these samples was assayed for radioactivity by liquid scintillation counting.

Figure 5:
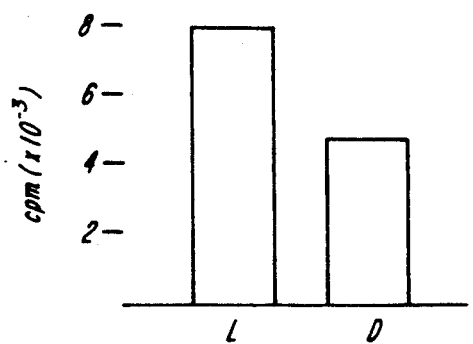
FIG. 5 is a bar graph depicting the results of substrate specificity experiments in which $^3$H- $PIP_2$ is incorporated into stripped ROS membranes which are then reconstituted with A-protein and PL-C, and subjected to light (L) and to dark (D) conditions.

The results are shown in FIG. 5, which graphically shows counts per minute of released radioactivity for samples subjected to light (L) and for samples that remained dark (D); with background response being subtracted. The samples containing activated A-protein and PL-C were the only ones to demonstrate significant levels of PIP$_2$ hydrolysis. According to the measured data, at 30 minutes, the A-protein-containing "light" sample showed 24% of the available radioactive PIP$_2$ had been hydrolyzed. This activation of PIP$_2$ hydrolysis is direct evidence of PL-C activation by A-protein, since PIP$_2$ has been shown to be the specific and only substrate of PL-C. The greater release of radioactivity in the light-exposed sample compared to the "dark" sample is a demonstration that this process is receptor mediated.

4. Production of Hybridoma and Monoclonal Antibody to A-Protein

Balb/c mice (The Jackson Laboratory, Bar Harbor, Me; 6-8 weeks old ) are immunized with four injections of A-protein. The injections are performed one week apart and 1 mg A-protein is injected on each occasion. The first three injections are given intraperitoneally, and the fourth intravenously. A-protein is injected with complete Freunds adjuvant on the first occasion, incomplete adjuvant on the second and third occasions, and without adjuvant on the last occasion. Serum withdrawn prior to the last injection shows prominent binding to purified A-protein using a solid phase microtiter plate enzyme-linked immunoassay. The mouse with the best immune response is sacrificed three days after the last injection.

Hybridomas are produced by fusion of spleen cells from the sacrificed mouse with NS-1 (P3NS-1/1-Ag4-1) myeloma cells (American Type Culture Collection, Rockville, MD; Acc. No. TIB18). In the present example, the method of Nadakavukaren (*Differentiation* 27: 209-202, (1984)) is employed to perform the fusions. Resultant clones are tested for binding to A-protein. Subcloning by serial dilution is carried out on one clone. The most productive subclone is injected into the peritoneal cavity of Balb/c mice to produce ascites fluid containing monoclonal antibody. The ascites fluid which is obtained is centrifuged, tested for activity, and then stored at −70° C. until required.

B. Antibody Typing

The anti-A-protein antibody is screened for antibody isotype by the Ouchterlony double diffusion test in agar plates against anti IgM, anti IgG, anti IgG1, anti IgG2a, anti IgG2b and anti IgG3 antibodies (Cappell).

The invention may be embodied in other specific forms without departing from the spirit or essential characteristics thereof. The present examples are therefore to be considered in all aspects as illustrative and not restrictive, the scope of the invention is indicated by the claims rather than by the foregoing description, and all changes which come within the meaning and range of equivalency of the claims are therefore intended to be embraced therein.

What is claimed is:

1. A method of inhibiting inositol metabolism in a cell comprising the step of introducing into said cell a binding molecule which reduces inositol metabolism by reaction with A-protein or an A-protein-containing complex, said binding molecule being a monoclonal antibody specifically reactive with A-protein.

2. The method of claim 1 wherein said introducing step comprises contacting said cell with a liposome containing said monoclonal antibody.

* * * * *